United States Patent [19]

Bátori et al.

[11] Patent Number: 4,871,846

[45] Date of Patent: Oct. 3, 1989

[54] PROCESS FOR THE PREPARATION OF CONDENSED AS-TRIAZINE DERIVATIVES

[75] Inventors: Sándor Bátori; György Hajós; András Messmer; Pál Benkó; László Pallos; Lujza Petöcz; Katalin Grasser; Ibolya Kosóczky; Enikö Szirt née Kiszelly, all of Budapest, Hungary

[73] Assignee: EGIS Gyogyszergyar, Budapest, Hungary

[21] Appl. No.: 43,600

[22] Filed: Apr. 28, 1987

[30] Foreign Application Priority Data

May 6, 1986 [HU] Hungary ............... 1857/86

[51] Int. Cl.⁴ .......................................... C07D 253/08
[52] U.S. Cl. .................................................. 544/183
[58] Field of Search .......................... 514/243; 544/183

[56] References Cited

U.S. PATENT DOCUMENTS

| | | | |
|---|---|---|---|
| 4,419,355 | 12/1983 | Kosoczky et al. | 544/183 |
| 4,602,018 | 7/1986 | Messmer et al. | 544/183 |
| 4,697,013 | 9/1987 | Messmer et al. | 544/183 |

FOREIGN PATENT DOCUMENTS

| | | | |
|---|---|---|---|
| 2081261 | 2/1982 | United Kingdom | 514/243 |
| 2146988 | 5/1985 | United Kingdom | 514/243 |
| 2155920 | 10/1985 | United Kingdom | 514/243 |

Primary Examiner—John M. Ford
Attorney, Agent, or Firm—Keil & Weinkauf

[57] ABSTRACT

A process for the preparation of condensed as-triazinium derivatives of the formula I

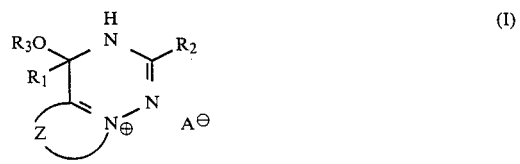

and isomers thereof, wherein $R_1$ inter alia is an alkyl group, $R_2$ inter alia is hydrogen or an alkyl group and $R_3$ is hydrogen and where Z is a group of the formula a or b

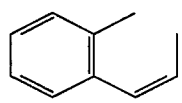
(a)

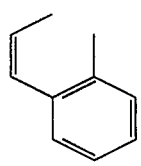

(b)

which comprises reacting a compound of the formula II

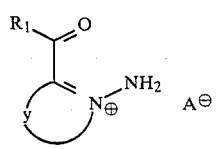
(II)

where Y is a group of the formula c or d

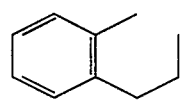
(c)

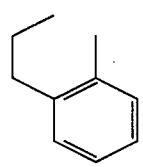

(d)

with a compound of the formula IIa $$NH_2-CO-R_2 \quad (IIa)$$

in the presence of a dehydrating agent. The advantage of the process is that it consists of fewer reaction steps and provides higher yields than the known methods. The compounds of formula I are pharmaceutically active known derivatives.

6 Claims, No Drawings

PROCESS FOR THE PREPARATION OF CONDENSED AS-TRIAZINE DERIVATIVES

This invention relates to a new and improved process for the preparation of pharmaceutically active known condensed as-triazine derivatives.

According to the present invention there is provided a process for the preparation of condensed as-triazinium derivatives of the general Formula I

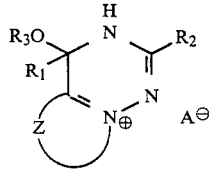
(I)

and isomers thereof
(wherein
$R_1$ stands for $C_{1-10}$ alkyl, phenyl or naphthyl whereby the two latter groups may optionally bear one or more identical or different halo, nitro, amino, hydroxy, $C_{1-4}$ alkyl and/or $C_{1-4}$ alkoxy substituent(s);
$R_2$ stands for hydrogen, halogen, hydroxy, $C_{1-4}$ alkyl, phenyl or naphthyl whereby the two latter groups may optionally bear one or more identical or different halo, nitro, amino, hydroxy, $C_{1-4}$ alkyl and/or $C_{1-4}$ alkoxy substituent(s);
$R_3$ represents hydrogen or $C_{1-4}$ alkyl;
Z stands for a group of the Formula (a)

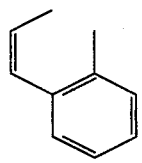
(a)

or (b)

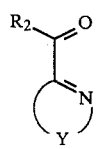
(b)

and
$A^-$ is an anion),
which comprises
(a) for the preparation of compounds of the general Formula I, wherein $R_3$ stands for hydrogen,
(a₁) reacting an oxo compound of the general Formula III

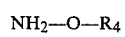
(III)

with an O-substituted hydroxyl amine of the general Formula IV $NH_2-O-R_4$ (IV)

and cyclising the compound of the general Formula II

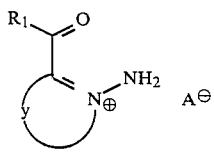
(II)

thus obtained—without or after isolation—with a compound of the general Formula IIa $NH_2-CO-R_2$ (IIa)

in the presence of a dehydrating agent; or
(a₂) cyclising a compound of the general Formula II with a compound of the general Formula IIa in the presence of a dehydrating agent; or
(a₃) reacting an imide of the general Formula V

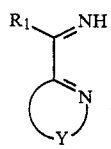
(V)

with a carboxylic acid of the general Formula VI $R_2-\underset{\underset{O}{\|}}{C}-OH$ (VI)

or a reactive functional derivative thereof, reacting the acyl imide of the general Formula VII

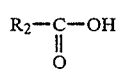
(VII)

thus obtained with an O-substituted hydroxyl amine of the general Formula IV and cyclising the compound of the general Formula VIII

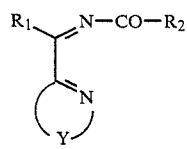
(VIII)

thus obtained—without or after isolation—in the presence of a dehydrating agent; or
(a₄) reacting an acyl imide of the general Formula VII with an O-substituted hydroxyl amine of the general Formula IV and cyclising the compound of the general Formula VIII thus obtained—without or after isolation—in the presence of a dehydrating agent; or
(a₅) cyclising a compound of the general Formula VIII in the presence of a dehydrating agent; or
(b) for the preparation of compound of the general Formula I, wherein $R_3$ stands for hydrogen and $R_2$ represents hydrogen, $C_{1-4}$ alkyl or unsubstituted phenyl, (b₁) reacting a compound of the general Formula II with an ortho ester of the general Formula IX $$R'_2C(OR_5)_3 \qquad (IX)$$

and cyclising the formimino ether of the general Formula X

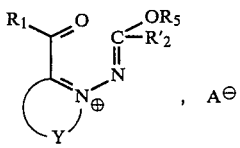

thus obtained by treating with ammonia; or (b₂) cyclising a formimino ether of the general Formula X by treatment with ammonia; or (c) for the preparation of compounds of the general Formula I, wherein R₃ stands for hydrogen and R₂ represents halogen, reacting a compound of the general Formula II with urea in the presence of a halogen-containing dehydrating agent; or (d) for the preparation of compounds of the general Formula I, wherein R₃ is C₁₋₄ alkyl, alkylating the corresponding compound of the general Formula I, wherein R₃ is hydrogen;

and, if desired, separating a compound of the general Formula I thus obtained into the isomers thereof and/or, if desired, exchanging an A⁻ anion for another A⁻ anion (wherein in the above general Formulae R₁, R₂ and A⁻ are as stated above, Y stands for a group of the Formula c or d;

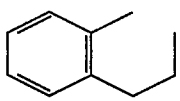

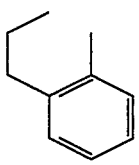

R₄ stands for an electron attracting group;

R'₂ represents hydrogen, C₁₋₄ alkyl or unsubstitued phenyl and

R₅ is C₁₋₄ alkyl).

The compounds of the general Formula I are known derivatives which exhibit valuable effects on the central nervous system (DOS No. 3,434,597).

According to methods (a₁) and (a₂) of the process of the present invention compounds of the general Formula I, wherein R₃ stands for hydrogen, are prepared by reacting an oxo compound of the general Formula II with an O-substituted hydroxyl amine of the general Formula IV and cyclising the compound of the general Formula II thus obtained with a compound of the general Formula IIa in the presence of a dehydrating agent.

In the first step of the above method it is preferred to use as starting material a compund of the general Formula IV wherein R₄ stands for alkylsulfonyl or arylsulfonyl, particularly methanesulfonyl, benzenesulfonyl, p-bromo-phenylsulfonyl or p-toluenesulfonyl. The reaction of the compounds of the general Formulae III and IV may be preferably carried out in an inert organic solvent.

The N-amino compound of the general Formula II thus obtained is reacted with a compound of the general Formula IIa in the presence of a dehydrating agent. It is preferred to use a Lewis acid (e.g. titanium tetrachloride, aluminium chloride or boron trifluoride) or a phosphorous oxyhalide (e.g. phosphorous oxychloride) as dehydrating agent. The reaction can be accomplished at a temperature between 40° C. and 140° C., preferably at 80°–100° C. As reaction medium inert organic solvents may serve, e.g. a halogenated hydrocarbon (e.g. chloroform, chlorobenzene etc.), an aromatic hydrocarbon (e.g. xylene, toluene, benzene etc.), a dialkyl amide (e.g. dimethyl formamide etc.), a dialkyl sulfoxide (e.g. dimethyl sulfoxide etc.), a cyclic or aliphatic ether (e.g. dioxane or diethyl ether) or acetonitrile. The excess of the liquid acid amide of the general Formula IIa (e.g. formamide) used may act as reaction medium as well.

According to a further method of the present invention (a₃–a₅) an imide of the general Formula V is reacted with a carboxylic acid of the general Formula VI or a reactive functional derivative thereof, the acyl imide of the general Formula VII thus obtained is reacted with an O-substituted hydroxyl amine of the general Formula IV and the compound of the general Formula VIII thus obtained is cyclised in the presence of a dehydrating agent.

As functional reactive derivative of a carboxylic acid of the general Formula VI preferably the corresponding acid halide, ester, anhydride or mixed anhydride may be used. The reaction of a compound of the general Formula VI or a reactive derivative thereof may be preferably carried out in the presence of a dehydrating agent. The acyl imide of the general Formula VII thus obtained is reacted with a compound of the general Formula IV, whereupon the N-amino-N'-acylimide of the general Formula VIII thus obtained is subjected to cyclisation, without or after isolation, in the presence of a dehydrating agent. In the above steps one may use as dehydrating agent preferably a Lewis acid (e.g. titanium tetrachloride, aluminium chloride, boron trifluoride etc.) or a phosphorous oxyhalide (e.g. phosphorous oxychloride etc.). The reaction may be accomplished at a temperature of 40°–160° C., preferably at 80°–110° C., in an inert organic solvent.

According to method (b) of the present invention compounds of the general Formula I, wherein R₃ stands for hydrogen and R₂ represents hydrogen, C₁₋₄ alkyl or unsubsituted phenyl, may be prepared by reacting a compound of the general Formula II with an ortho ester of the general Formula IX and treating the iminoether of the general Formula X thus obtained with ammonia.

The ortho ester of the general Formula IX is selected by taking into consideration the definition of symbol R₂ in the compound of the general Formula I sought to be prepared. Thus, if compounds of the general Formula I, wherein R₂ represents hydrogen, are to be prepared, an alkyl ortho formiate of the general Formula IX is used. The reaction of the compounds of the general Formulae II and IX may be carried out in an inert solvent. It is preferred to use a nitrile (e.g. acetonitrile), or aromatic hydrocarbon (e.g. benzene or toluene) or an excess of the liquid compound of the general Formula IX as reaction medium. The reaction may be carried out preferably at elevated temperature, particularly at the boiling point of the reaction mixture, but one may work at lower temperatures as well.

The imino ether of the general Formula X thus obtained is reacted with ammonia preferably in an inert organic solvent. It is preferred to use an alcohol as reaction medium. The reaction may be accomplished at a temperature of 10°–40° C., preferably at room temperature. The ammonia may be used in equimolar amount or in a small excess of some molar %.

According to method (c) of the present invention compounds of the general Formula I, wherein $R_3$ stands for hydrogen and $R_2$ represents halogen, may be prepared by reacting a compound of the general Formula II with urea in the presence of a halogen-containing dehydrating agent. As halogen-containing dehydrating agent preferably phosphorous oxychloride may be used. As reaction medium preferably solvents having a high boiling point—particularly those boiling above 100° C.—may serve. The excess of the halogen-containing dehydrating agent (e.g. phosphorous oxychloride) may also act as reaction medium.

According to method (d) compounds of the general Formula I, wherein $R_3$ stands for $C_{1-4}$ alkyl, are prepared by alkylating a compound of the general Formula I wherein $R_3$ represents hydrogen. The said alkylation is carried out by methods known per se. One may proceed preferably by carrying out alkylation with the corresponding alkali alcoholate in alcoholic medium. Thus methylation can be preferably performed by using an alkali methylate in methanol as medium.

A compound of the general Formula I obtained by any of the above methods in the form of an isomer mixture can be separated, if desired, into the isomers by methods known per se.

In a compound of the general Formula I thus obtained the $A^-$ anion may be exchanged for an other $A^-$ anion by methods known per se.

According to a particularly preferred embodiment of the process of the present invention compounds of the general Formula I are prepared wherein $R_1$ stands for 4-chlorophenyl, $R_2$ and $R_3$ are hydrogen and Z is a group of the Formula (a). Thus the process of the present invention is particularly suitable for the preparation of 1-hydroxyl-1-(4-chlorophenyl)-1,2-dihydro-as-triazino[6,1-a]isoquinolinium salts.

The term "alkyl" used throughout the specification relates to straight or branched chain alkyl groups (e.g. methyl, ethyl, n-propyl, isopropyl, etc.). The term "alkoxy" relates to alkylether groups comprising the above straight or branched chain alkyl grups (e.g. methoxy, ethoxy, n-propoxy, isopropoxy etc.). The term "halogen" encompasses the fluorine, chlorine, bromine and iodine atoms.

$A^-$ stands preferably for the anion of a pharmaceutically acceptable inorganic or organic acid, e.g. chloride, bromide, iodide, perchlorate or acetate, lactate, maleate, fumarate, ethanesulfonate etc.

From the starting materials used the compounds of the general Formula III, wherein $R_1$ stands for p-chlorophenyl and Y is a group of the Formula (c) is known [E. Spath and collaborators: Ber. 63, 134 (193)].

The starting materials of the general Formulae II, V, VII, VIII and X are new compounds.

According to a further aspect of the present invention there are provided new compounds of the general Formulae II, V, VII, VIII and X.

The process of the present invention directed to the preparation of the compounds of the general Formula I shows several advantages over the known methods.

Thus the compounds of the general Formula I can be prepared by the process of the present invention starting from the dihydro-N-amino-compounds of the general Formula II by less reaction-steps and with higher yields than according to DOS No. 3,434,597 (see the comparison of Example 2 of the present patent application and Example 3 of DOS No. 3,434,597). The yield of the one-step cyclisation of the dihydro-N-amino compound of the general Formula II also surpasses that disclosed in DOS No. 3,434,597 (see a comparison of Examples 1, 3 and 4 of the present patent application with Examples 5 and 6 of DOS No. 3,434,597).

Further details of the present invention are to be found in the following Examples without limiting the scope of protection to the said Examples.

EXAMPLE 1

Preparation of 1-hydroxy-1-(4-chlorophenyl)-1,2-dihydro-as-triazino[6,1-a]isoquinolinium chloride To a mixture of 11 ml of dioxane and 3.8 g (0.002 mole) of titanium tetrachloride at room temperature 1.92 g (0.005 mole) of 2-amino-1-(4-chlorobenzoyl)-3,4-dihydro-isoquinolinium perchlorate are added. The reaction mixture is heated to boiling while 3.4 g (0.075 mole) of formamide are added within an hour. The reaction mixture is cooled and admixed with 5 ml of concentrated hydrochloric acid and water. The crystalline desired product precipitates, yield 85%, m.p.: 227°–228° C.

The starting material can be prepared as follows:

10.5 g (0.039 mole) of 1-(4-chlorobenzoyl)-3,4-dihydro-isoquinoline are dissolved in dichloromethane whereupon a solution of 7.3 g (0.039 mole) of O-(p-toluenesulfonyl)-hydroxyl amine in dichloromethane is added under ice cooling. The reaction mixture is stirred at 0° C. for half an hour and at room temperature for 2 hours and evaporated to dryness. The residue is dissolved in acetonitrile containing 20% of water under warming, whereupon to the solution 10 ml of 70% perchloric acid and water are added. On cooling crystalline 2-amino-1-(4-chlorobenzoyl)-3,4-dihydro-isoquinolinium-perchlorate precipitates, yield 56%, m.p.: 214°–216° C.

EXAMPLE 2

Preparation of 1-hydroxy-1-(4-chloro-phenyl)-1,2-dihydro-as-triazino[6,1-a]isoquinolinium perchlorate A mixture of 4.57 g (0.01 mole) of 2-amino-1-(4-chlorobenzoyl)-3,4-dihydro-isoquinolinium-tosylate, 4.45 g (0.03 mole) of ethyl ortho formiate and acetonitrile is heated to boiling for an hour. The reaction mixture is cooled and the product—i.e. 1-(4-chlorobenzoyl)-2-[N-(ethoxyiminoformyl)]-3,4-dihydro-isoquinolinium-tosylate—is reacted under introducing ammonia gas, whereupon the solvent is removed and the residue is treated with 5 ml of 70% perchloric acid. The mixture is extracted with nitromethane and the solvent is removed. The desired compound is obtained with a yield of 50%, m.p.: 239°–240° C.

EXAMPLE 3

Preparation of
1-hydroxy-1-phenyl-1,2-dihydro-as-triazino[6,1-a]isoquinolinium-perchlorate A mixture of 10.15 g (0.024 mole) of 2-amino-1-benzoyl-3,4-dihydro-isoquinolinium-tosylate, 30 ml of formamide and 15 ml of phosphorous oxychloride is heated at 80°–90° C. The reaction mixture is cooled, diluted with water, whereupon 10 ml of 70% perchloric acid are added. The desired compound is obtained with a yield of 65%, m.p.: 245°–256° C.

EXAMPLE 4

Preparation of
4-hydroxy-4-(4-chlorophenyl)-3,4-dihydro-as-triazino[6,1-a]quinolinium perchlorate A mixture of 4.57 g (0.01 mole) of 1-amino-2-(4-chlorobenzoyl)-3,4-dihydro-quinolinium-tosylate, 30 ml of formamide and 20 ml of phosphorous oxychloride is heated at 90° C. for an hour. The reaction mixture is poured into water and after an hour 5 ml of 70% perchloric acid are added. The desired compound is obtained with a yield of 78%, m.p.: 293°–294° C.

EXAMPLE 5

Preparation of
1-(4-chlorophenyl)-1-hydroxy-1,2-dihydro-as-triazino[6,1-a]isoquinolinium-ethanesulfonate 4.1 g (0.01 mole) of 1-(4-chlorophenyl)-1-hydroxy-1,2-dihydro-as-triazino[6,1-a]isoquinolinium-perchlorate are dissolved in 50 ml of acetonitrile and 2.2 g (0.02 mole) of ethanesulfonic acid are added. The reaction mixture is evaporated and the residue is dissolved in ethyl acetate. The solution is cooled, the precipitated product is filtered off. The desired compound is obtained with a yield of 85%, m.p.: 187°–188° C.

EXAMPLE 6

Preparation of
1-(4-chlorophenyl)-1-methoxy-1,2-dihydro-as-triazino[6,1-a]isoquinolinium perchlorate A mixture of 9.1 g (0.02 mole) of 1-(4-chlorobenzoyl)-2-amino-3,4-dihydro-isoquinolinium-tosylate, 30 ml of formamide and 15 ml of phosphorous oxychloride is heated at 80°–90° C. The reaction mixture is cooled and a methanolic solution of 0.4 mole of sodium methylate is added. The product is precipitated by adding 16 ml of a 7% aqueous perchloric acid solution. The desired compound is obtained with a yield of 81%, m.p.: 158°–159° C.

What we claim is:

1. The process for the preparation of a condensed as-triazine derivative of the formula I

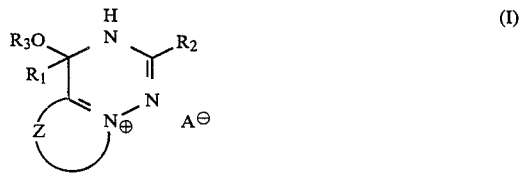

and isomers thereof where $R_1$ is $C_{1-10}$ alkyl, phenyl or naphthyl, wherein the two latter groups may optionally bear one or more identical or different halo, nitro, amino, hydroxy, $C_{1-4}$ alkyl and/or $C_{1-4}$ alkoxy substituent(s);

$R_2$ is hydrogen, halogen, hydroxy, $C_{1-4}$ alkyl, phenyl or naphthyl, wherein the two latter groups may optionally bear one or more identical or different halo, nitro, amino, hydroxy, $C_{1-4}$ alkyl and/or $C_{1-4}$ alkoxy substituent(s);

$R_3$ is hydrogen;

Z is a group of the formula (a)

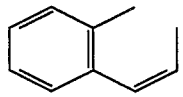

or (b)

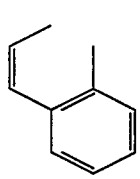

and $A^-$ is an anion, which comprises: reacting a compound of the formula II

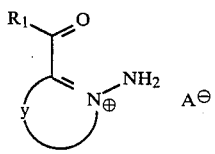

where Y is a group of the formula c or d

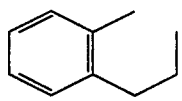

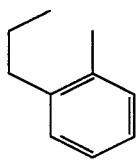

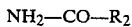

with the compound of the formula IIa $$NH_2-CO-R_2 \qquad (IIa)$$

in the presence of a dehydrating agent.

2. The process of claim 1, wherein the reaction is carried out in an inert organic solvent.

3. The process of claim 1, wherein the dehydrating agent is a Lewis acid or a phosphorous oxyhalide.

4. The process of claim 1, wherein the dehydrating agent is titanium tetrachloride, aluminum chloride, boron trifluoride or phosphorous oxychloride.

5. The process of claim 1, wherein $R_1$ is 4-chlorophenyl, $R_2$ and $R_3$ are hydrogen and Z is a group of the formula (a).

6. The process of claim 1, wherein 1-hydroxy-1-(4-chlorophenyl)-1,2-dihydro-as-triazino[6,1-a]isoquinolinium salts are prepared.

* * * * *